(12) United States Patent
Zhang et al.

(10) Patent No.: US 10,814,314 B2
(45) Date of Patent: Oct. 27, 2020

(54) CATALYST FOR AMINATING POLYETHER POLYOL AND PREPARATION METHOD THEREOF AND METHOD OF PREPARING POLYETHERAMINES USING CATALYST THEREOF

(71) Applicant: Wanhua Chemical Group Co., Ltd., Yantai (CN)

(72) Inventors: Congying Zhang, Yantai (CN); Shujie Ren, Yantai (CN); Xin Li, Yantai (CN); Zhenguo Liu, Yantai (CN); Xiaolong Wang, Yantai (CN); Ningning Wang, Yantai (CN); Hao Chen, Yantai (CN); Yuan Li, Yantai (CN); Xueli Yu, Yantai (CN); Jinhong Song, Yantai (CN)

(73) Assignee: Wanhua Chemical Group Co., Ltd. (CN)

( * ) Notice: Subject to any disclaimer, the term of this patent is extended or adjusted under 35 U.S.C. 154(b) by 0 days.

(21) Appl. No.: 15/772,442

(22) PCT Filed: Nov. 13, 2015

(86) PCT No.: PCT/CN2015/094535
§ 371 (c)(1),
(2) Date: Apr. 30, 2018

(87) PCT Pub. No.: WO2017/079965
PCT Pub. Date: May 18, 2017

(65) Prior Publication Data
US 2018/0318806 A1    Nov. 8, 2018

(30) Foreign Application Priority Data

Nov. 9, 2015 (CN) .......................... 2015 1 0753187

(51) Int. Cl.
| | | |
|---|---|---|
| *B01J 23/89* | (2006.01) | |
| *C07C 213/02* | (2006.01) | |
| *C08G 65/325* | (2006.01) | |
| *B01J 23/72* | (2006.01) | |
| *B01J 23/44* | (2006.01) | |
| *C07C 217/08* | (2006.01) | |
| *B01J 23/755* | (2006.01) | |
| *B01J 37/02* | (2006.01) | |

(52) U.S. Cl.
CPC ........... *B01J 23/8993* (2013.01); *B01J 23/44* (2013.01); *B01J 23/72* (2013.01); *B01J 23/755* (2013.01); *B01J 23/894* (2013.01); *B01J 23/898* (2013.01); *B01J 23/8926* (2013.01); *B01J 23/8953* (2013.01); *B01J 23/8966* (2013.01); *B01J 23/8973* (2013.01); *B01J 37/0201* (2013.01); *B01J 37/0236* (2013.01); *C07C 213/02* (2013.01); *C07C 217/08* (2013.01); *C08G 65/325* (2013.01); *C08G 2650/10* (2013.01); *C08G 2650/50* (2013.01)

(58) Field of Classification Search
CPC ...................................................... B01J 23/44
USPC ....................................................... 564/475
See application file for complete search history.

(56) References Cited

U.S. PATENT DOCUMENTS

| | | |
|---|---|---|
| 3,128,311 A | 4/1964 | Shirley |
| 4,766,245 A | 8/1988 | Larkin et al. |
| 2010/0069671 A1 | 3/2010 | Buehring et al. |

FOREIGN PATENT DOCUMENTS

| | | |
|---|---|---|
| CN | 1546550 A | 11/2004 |
| CN | 102161822 A | 8/2011 |
| CN | 102336903 A | 2/2012 |
| CN | 102875795 A | 1/2013 |
| CN | 103145974 A | 6/2013 |
| CN | 102382294 B | 11/2013 |
| CN | 103709391 A | 4/2014 |
| CN | 104119239 A | 10/2014 |
| CN | 104475118 A | 4/2015 |
| EP | 0828558 A1 | 3/1998 |
| JP | H0920735 A | 1/1997 |
| WO | 9730103 A2 | 8/1997 |

OTHER PUBLICATIONS

Search Report from European Application No. 15908095 1 dated Aug. 21, 2018.
International Search Report from PCT/CN2015/094535, dated Jun. 23, 2016, pp. 1-2.

*Primary Examiner* — Ana Z Muresan
(74) *Attorney, Agent, or Firm* — Lerner, David, Littenberg, Krumholz & Mentlik, LLP

(57) ABSTRACT

The present invention relates to a catalyst for aminating a polyether polyol and preparation method thereof and a method of preparing a polyetheramine using the catalyst. The catalyst has active components and a carrier. The active components are Ni, Cu, and Pd. The method of preparing the catalyst comprises the following steps: using a metal solution or a metal melt impregnated carrier, obtaining a catalyst precursor; and drying and calcinating the obtained catalyst precursor, so as to obtain a catalyst. By introducing the active component Pd in the catalyst, the present invention clearly improves selectivity of an amination catalyst with respect to a preaminated product, and increases raw material conversion rate.

17 Claims, No Drawings

CATALYST FOR AMINATING POLYETHER POLYOL AND PREPARATION METHOD THEREOF AND METHOD OF PREPARING POLYETHERAMINES USING CATALYST THEREOF

CROSS REFERENCE TO RELATED APPLICATIONS

The present application is a national phase entry under 35 U.S.C. § 371 of International Application No. PCT/CN2015/094535, filed Nov. 13, 2015, which claims priority from Chinese Patent Application No. 201510753187.7 filed Nov. 9, 2015, all of which are hereby incorporated herein by reference.

TECHNICAL FIELD

The present invention relates to a catalyst for aminating a polyether polyol and a preparation method thereof and a method for preparing polyetheramines using the catalyst; the present invention belongs to the field of catalyst and the field of polymer materials.

TECHNICAL BACKGROUND

Amino-terminated alkylene oxide polymers, also known as polyetheramines, are polymers with a backbone that is polyether structure and terminal active groups that are amino groups. Most of these compounds are polyetheramines with terminal active groups that are amino groups, which are obtained through the chemical reaction treatment of the terminal active groups, hydroxyl groups, using ring-opening polymers of epoxy compounds corresponding to their structures (also referred to as polyether polyols) as raw materials. Compared with the traditional amine epoxy curing agent, polyetheramine, due to the ether bond in the structure, which improves the toughness of the cured product while maintaining low toxicity, has been used increasingly, and has gathered interest in the building industry and material industry.

Polyetheramine products with small molecular weight (Mw<500), due to their small molecular weight, the products have low viscosity, are not easy to crystallize under low temperature and have good construction performance; they are usually used in the manufacture of large devices that are composed of epoxy resin composite materials which are difficult to process, and because of their good fluidity, they have high construction efficiency and success rate. At the same time, for the north of China, where the construction temperature fluctuates largely and the temperature is relatively low, the series products are mainly used. For polyetheramine products with larger molecular weight, due to their long carbon chain backbone and rich ether linkages, the products have good flexibility, and is usually used in the field of polyurea resin.

The synthesis methods of polyetheramines mainly comprise reductive amination method, leaving group method and polyether nitrile reduction method. Among them, the reductive amination method is also known as hydrogen-presented amination method, the process of the method is the most advanced, while the quality of the products is the most stable, and the products are more in line with environmental requirements, thus it has become the main production methods of industrialization of polyetheramines at home and abroad.

U.S. Pat. No. 3,128,311 uses a trimetallic catalyst system of Ni, Cu and one metal selected from the group consisting of Cr, Ti, Zn and Mn for the amination of fatty alcohols. The manufacturing process of this trimetallic catalyst is complicated, the strength of the catalyst is poor and the catalyst is prone to pulverization, which is not conducive to amination reaction.

U.S.20100069671 uses a catalyst that comprises at least 80 wt % of Co and Al and less than 5 wt % of Cu metal to catalyze the corresponding polyether polyols to prepare polyetheramines, the catalyst is suitable for polyether polyols with larger molecular weights, and it cannot be used for the animation of polyether polyols with molecular weights that are less than 500.

CN201110188776 discloses an animation process for polyether polyols with molecular weights that are above 100, the process adopts skeletal nickel catalyst, the content of Ni is 85-95 wt % and the content of Al is 5-15 wt %. The process is the kettle batch production process, the catalyst can be recycled, due to the batch operation, there's large fluctuation in the product quality, meanwhile, the method uses skeletal nickel catalyst, in the actual industrial production process, the skeletal nickel catalyst is air-sensitive and extremely flammable, there are greater safety risks and hidden danger in the storage, loading, use and retirement process of the catalyst.

CN201110259396.8 discloses a one-pot process for preparing polyetheramine series products, the process is the same as that in CN201110188776, using a batch process. Polypropylene glycol, catalyst and cocatalyst are fed into an autoclave, and the autoclave is filled with a certain amount of ammonia and hydrogen to produce polyether amine product in a one-pot reaction. With the total mass of all the components in the catalyst being calculated as 100%, the catalyst comprises, by mass, 1 to 5% of aluminum, 90 to 95% of nickel and 1 to 3% of tin, respectively; or the catalyst comprises, by mass, 10-15% of aluminum, 80-90% of nickel, 3-6% of iron and 1-3% of chromium, respectively; and the cocatalyst is any one of sodium carbonate, sodium bicarbonate, sodium hydroxide, potassium carbonate, potassium bicarbonate, potassium hydroxide, calcium hydroxide or monopotassium phosphate; the quality of the polyether amine prepared by the method fluctuates greatly and the highest conversion rate of the raw materials of the product obtained by the method only reaches 95%.

CN200310112615.5 discloses a process for preparing polyetheramines by hydrogen-present amination method of bifunctional polyether with molecular weight of 2000 and trifunctional polyether with molecular weight of 5000. Using skeletal nickel catalyst, Ni accounts for 60-80 wt %, Al accounts for 10-35 wt %, Cr accounts for 2-10 wt %. The catalyst is not suitable for the preparing process of polyetheramines by amination of polyether polyols containing multiple monomer backbones such as ethylene oxide (EO) and/or propylene oxide (PO) and for polyether polyols having an average molecular weight less than 500.

U.S. Pat. No. 4,766,245 discloses an amination reaction of a hydroxyl-terminated polyether having a molecular weight of more than 500. The catalyst consists of 60-75 wt % of Ni and 25-40 wt % of Al, and the reaction temperature is 235-250° C. and the pressure is 14-19 MPa; the catalyst is only suitable for the amination of polyether polyols with a molecular weight of more than 500, and is not suitable for polyether polyols with an average molecular weight of less than 500.

SUMMARY OF THE INVENTION

Therefore, one of the objects of the present invention is to provide a catalyst which is suitable not only for amination of a polyether polyol having a relatively large molecular weight, but also for amination of a polyether polyol having a molecular weight of less than 500; the catalyst not only can improve the selectivity and reduce the by-products generated during the reaction, but also can increase the yield of polyetheramine products.

Another object of the present invention is to provide a method for preparing the catalyst.

A further object of the present invention is to provide a method for preparing polyetheramines using the catalyst.

In order to achieve the above objects, the present invention adopts the following technical solutions: a catalyst for aminating a polyether polyol comprising a carrier and active components, and the active components are Ni, Cu and Pd.

Based on the total weight of the catalyst, the content of the active components of the catalyst are as follows:
the content of Ni element is from 5 wt % to 30 wt %, preferably from 7 wt % to 25 wt %, particularly preferably from 10 wt % to 20 wt %;
the content of Cu element is from 5 wt % to 25 wt %, preferably from 7 wt % to 20 wt %, particularly preferably from 8 wt % to 15 wt %;
the content of Pd element is from 0.3 wt % to 2.0 wt %, preferably from 0.5 wt % to 1.5 wt %.

The catalyst also includes promoters.

The promoters comprise a first promoter selected from the group consisting of V, Cr, Mn, Fe, Co, Zn, Y, Mo, W, Sn, Pb and Bi elements, and a mixture of more thereof; preferably selected from the group consisting of Co, Zn and Mo, and a mixture of more thereof; and more preferably Zn and/or Mo.

Based on the total weight of the catalyst, the content of the first promoter is from 0 wt % to 5 wt %, preferably from 2 wt % to 4 wt %.

The promoters further comprise a second promoter selected from the group consisting of La, Ce, Nd and Sm elements, and a mixture of more thereof, preferably selected from the group consisting of La, Ce and Nd, and a mixture of more thereof.

Based on the total weight of the catalyst, the content of the second promoter is 0 wt % to 2 wt %, preferably 0.5 wt % to 1.5 wt %.

The balance of the catalyst is a carrier. The carrier is a porous oxide.

The porous oxide is selected from the group consisting of MgO, $Al_2O_3$, $SiO_2$, $TiO_2$ and $ZrO_2$, and a mixture of more thereof, preferably an $Al_2O_3$ porous carrier. The shape of the carrier can be any shape, and the specific shape of the carrier can be designed and selected according to the reactor for catalyzing different polyether polyols and aminating agents (for example, according to the actual requirement, the reactor can be a slurry reactor, a fixed bed reactor, a fluidized bed reactor, a tubular reactor or a bubble column reactor etc.), comprising but is not limited to one or two or more of flake, strip, clover and the like.

A preparation method of a catalyst for aminating a polyether polyol comprising the following steps:
1) impregnating the carrier with metal solutions or metal melts to obtain a catalyst precursor;
2) drying and calcinating the catalyst precursor to obtain the catalyst;
wherein the metal solutions are aqueous solutions of metal salts or aqueous solutions of metal salt complexes, the metal melts are molten metal salts, and the metals include active metals Ni, Cu and Pd.

The metal further comprises the first and second promoters selected from the group consisting of V, Cr, Mn, Fe, Co, Zn, Y, Mo, W, Sn, Pb, Bi, La, Ce, Nd and Sm, and a mixture of more thereof.

The metal salts include, but are not limited to the halides, nitrates, or organic acid salts of the above metals, preferably the nitrates, formates or oxalates of the metals, particularly preferably the nitrates of the metals; the metal salt complexes are water-soluble compounds formed by the action of inorganic acid salts or organic acid salts of the metals with a ligand, are preferably water-soluble metal salt complexes using ammonia or an organic amine as a ligand.

The impregnating described in step 1) can be impregnating the carrier with metal solutions or metal melts, or by spraying the metal solutions or metal melts on the carrier, or by depositing the metal solutions or metal melts on the carrier.

The impregnating process described in step 1) can be carried out in any manner, the carrier can be impregnated by the mixture of various metal salt solutions, or can be impregnated with different metal salt solutions separately. The impregnating process can be done in one step or in several steps. The metal salt solutions can be of any concentration, the catalyst of the present invention can be obtained by the impregnation of metal salt solutions with different concentrations in several steps.

The drying process of step 2) is carried out at 60° C.-150° C., preferably 80° C.-120° C.; drying time is 4 hrs-24 hrs, preferably 8 hrs-12 hrs; if necessary, the drying can be carried out under vacuum conditions, the degree of vacuum is 0.1 KPa-101 KPa, preferably 30 KPa-70 KPa. The calcination process is carried out at 100° C.-500° C., preferably 300° C.-500° C.; calcination time is 4 hrs-24 hrs, preferably 8 hrs-12 hrs.

The catalyst obtained in step 2) is reduced at 100° C.-250° C., preferably 120° C.-200° C. before being used for amination of polyether polyols; the reduction time is 8 hrs-24 hrs, preferably 12 hrs-24 hrs. A gas that contains hydrogen is used in the reduction process, such as pure hydrogen or a mixed gas of inert gas and hydrogen, the inert gas includes, but is not limited to nitrogen, helium, neon, argon or krypton etc., preferably nitrogen, and the volume content of the inert gas is from 5% to 95%; preferably from 50% to 95%.

A method for preparing polyetheramines by aminating a polyether polyol, comprises the following steps:
subjecting the polyether polyol to a reductive amination reaction in the presence of a hydrogen-containing gas, an aminating agent, and the catalyst of the present invention to prepare the polyetheramine.

In the present invention, the amination reaction can be intermolecular or intramolecular, and a cyclic compound is formed by the intramolecular amination. The terminal hydroxyl groups of the polyether polyol is replaced by aminos, primary or secondary amines, the polyetheramine with the corresponding terminal groups or the cyclic amide is obtained; the intramolecular amination can be, for example, amination of diglycol (diethylene glycol, DEG) to obtain diaminodiglycol ether, monoaminodiglycol ether and morpholine.

The catalysts according to the invention are particularly suitable for polyols with polyether as backbone units, preferably for polyols comprising ethylene oxide (EO) and/or propylene oxide (PO) backbone(s), with a molecular weight of 100-7000, preferably 106-5000, more preferably 200-500, and the polyether polyol comprises two or more hydroxyl groups.

In the present invention, the polyether polyols are usually prepared by the reaction of one or two or more of ethylene glycol, propylene glycol, glycerine, trimethylolpropane (TMP) and neopentyl glycol (NPG), which are used as the initiator, with PO and/or EO. The synthetic method is conventional and has been reported in a large amount of known documents. For details, reference can be made to China Invention Patent CN201210393578.9 and CN201310627712.1.

In the method for preparing polyetheramines by aminating the polyether polyol of the present invention, the aminating agent is an organic amine having no more than 10 carbon atoms or ammonia, the aminating agent has the general formula NHR1R2, wherein R1 and R2 are the same or different and are each independently selected from hydrogen, methyl, ethyl, propyl or isopropyl, preferably ammonia wherein R1 and R2 are hydrogen.

The method for preparing polyetheramines according to the present invention can be carried out intermittently or continuously, preferably continuously. The preparation of polyetheramines in a continuous manner is carried out in a tubular reactor in the form of a liquid phase reaction or a gas phase reaction.

In the present invention, the molar ratio of the aminating agent to the polyether polyol is (1-60):1, preferably (6-20):1. The molar ratio of hydrogen to the polyether polyol is (0.01-1):1, preferably (0.05-0.5):1.

The space velocity of the catalyst is from 0.01 to 3 liters of the polyether polyol per liter of the catalyst per hour, preferably from 0.1 to 1.0 liter of the polyether polyol per liter of the catalyst per hour.

The reaction temperature of the reductive amination reaction of the present invention is from 100° C. to 300° C., preferably from 150° C. to 250° C., particularly preferably from 180° C. to 230° C.; and the reaction pressure (absolute pressure) is from 0.1 MPa to 30 MPa, preferably from 0.1 MPa to 15 MPa.

The reductive amination process of the present invention may use a solvent including but is not limited to water, methanol, ethanol, benzene, cyclohexane, toluene, diethyl ether, THF, MTBE (methyl tert-butyl ether) and other alcohols, ethers, hydrocarbons. The reductive amination reaction of the present invention is preferably carried out without using a solvent.

The beneficial effects of the present invention are:

(1) It has been found in the course of the study of the present invention that by introducing another active component Pd on the basis of the active metals Ni and Cu, the selectivity of the catalyst to the expected aminated product and the conversion of the starting material are significantly increased; the catalyst with active metal Pd of the present invention exhibits excellent activity in the amination of polyether polyols having a molecular weight of 200-500. Using the catalyst of the present invention to catalyze the amination reaction of polyether polyols, especially for catalyzing the amination of polyether polyols having an average molecular weight of less than 500, the yields of the aminated product can reach to 97-100%, the conversion of the starting material can reach to 99-100%.

(2) when the content of Pd introduced is less than 0.3 wt %, a significant decrease of selectivity of the catalyst occurs during the amination process, especially for the polyether polyol having a molecular weight of less than 500; when the content of Pd is more than 2 wt %, increasing Pd content does not contribute to the improvement of activity and selectivity of the catalyst; for practical application and cost considerations, it is unnecessary and meaningless to continue to increase the content of Pd, therefore, the content of Pd in the catalyst is controlled to be 0.3 wt %-2.0 wt %, preferably 0.5 wt %-1.5 wt %.

(3) The addition of a first promoter element, such as Zn, effectively increases the selectivity of the catalyst; the addition of a second promoter element, such as Ce, can improve the anti-toxic, anti-carbonization of the catalyst and prolong the service life of the catalyst.

(4) The catalysts of the present invention show good mechanical properties and chemical stability during the entire life cycle of the amination reaction and overcome the defects of poor mechanical properties and easily being pulverized of the existing catalyst during use.

(5) Compared with the existing catalysts for amination comprising high content of metal, such as Ni and Co, the catalyst of the present invention can achieve the same activity and even higher activity with less amount of metal, reduce the overall cost of the catalyst.

(6) The catalysts of the present invention are safe and reliable during storage and use and are suitable for polyether polyols containing a wide variety of monomers (such as EO and PO).

EMBODIMENTS

The present invention will be further illustrated with the combination of the examples below, but the present invention is not limited to the listed examples, it should comprise the equivalent improvements and modifications to the technical solutions defined in the appended claims of the present application.

Gas chromatograph: Shimadzu GC-2014 (FID) detector, SE-30 capillary column (φ0.30 mm×30 m), inlet 270° C., detector 270° C.; temperature program: 70° C., constant temperature 1 min, then the temperature is increased to 240° C. at a rate of 40° C./min, the temperature is maintained for 5 min.

The reductive amination reactors in the embodiments are fixed bed reactors,

Methylamine, dimethylamine, polyether polyols (PPG-230, T-2000, D-5000, T-403): Wanhua Chemical Group CO., LTD;

Alumina extrudated article: Zibo Wufeng Aluminium Magnesium Technology Co., Ltd. series 4010-1;

Zirconium dioxide spherical carrier: Zhimo (Shanghai) New Material Technology Co., Ltd. series P1410;

Silicon dioxide spherical carrier: Evonik, series R974;

Alumina clover-type extrudated article containing 5% silicon: Zibo Jingcun Fine Chemical Co., Ltd.;

$TiO_2$ spherical carrier: Beijing Xin Yong Tai Chemical Additives Co., Ltd. A101;

MgO spherical carrier: Jiangxi Huihua Co., Ltd. series HHZT.

EXAMPLE 1

75 g of alumina extrudated articles (each article has a diameter of 1.5 mm) were dried at 120° C. for 12 hrs and then were poured into 75 ml of nitrate impregnation solution containing 16.5 g of Ni, 5 g of Cu, 1 g of Pd and 2.5 g of Cr, thoroughly mixed for 2 hrs at room temperature. After the above catalyst precursor was dried at 100° C. for 8 hrs and was calcinated at 400° C. for 4 hrs, it was cooled, 107.1 g of catalyst 1 containing 16.5% of Ni, 5% of Cu, 1% of Pd and 2.5% of Cr was obtained.

EXAMPLE 2

66.5 g of zirconium dioxide spherical carriers (each carrier has a diameter of 3 mm) were dried at 120° C. for 12 hrs and then were poured into 75 ml of oxalate impregnation solution containing 7 g of Ni, 20 g of Cu, 1.5 g of Pd, 4 g of Zn and 1 g of Ce, thoroughly mixed for 2 hrs at room temperature. After the above catalyst precursor was dried at 120° C. for 4 hrs and was calcinated at 475° C. for 12 hrs, it was cooled, 108.4 g of catalyst 2 containing 7% of Ni, 20% of Cu, 1.5% of Pd, 4% of Zn and 1% of Ce was obtained.

EXAMPLE 3

62.5 g of silicon dioxide spherical carriers (each carrier has a diameter of 2 mm) were dried at 100° C. for 24 hrs and then were poured into 65 ml of formate impregnation solution containing 5 g of Ni, 25 g of Cu, 2 g of Pd, 4 g of Co, 1 g of Zn and 0.5 g of La, thoroughly mixed for 2 hrs at room temperature. After the above catalyst precursor was dried at 60° C. for 24 hrs under vacuum and was calcinated at 300° C. for 18 hrs, it was cooled, 110.0 g of catalyst 3 containing 5% of Ni, 25% of Cu, 2% of Pd, 4% of Co, 1% of Zn and 0.5% of La was obtained.

EXAMPLE 4

60.5 g of alumina clover-type extrudated carriers containing 5% silicon (each carrier has a diameter of 3 mm) were dried at 110° C. for 10 hrs and then were poured into 60 ml of nitrate impregnation solution containing 30 g of Ni, 5 g of Cu, 0.5 g of Pd, 2 g of Sn, 1.5 g of Sm and 0.5 g of Ce, thoroughly mixed for 2 hrs at room temperature. After the above catalyst precursor was dried at 110° C. for 6 hrs under vacuum and was calcinated at 350° C. for 6 hrs, it was cooled, 110.4 g of catalyst 4 containing 30% of Ni, 5% of Cu, 0.5% of Pd, 2% of Sn, 1.5% of Sm and 0.5% of Ce was obtained.

EXAMPLE 5

64 g of $TiO_2$ spherical carriers (each carrier has a diameter of 3 mm) were dried at 90° C. for 6 hrs and then were poured into 65 ml of nitrate impregnation solution containing 25 g of Ni, 8 g of Cu, 1 g of Pd and 2 g of Mo, thoroughly mixed for 2 hrs at room temperature. After the above catalyst precursor was dried at 110° C. for 8 hrs and was calcinated at 425° C. for 6 hrs, it was cooled, 110.0 g of catalyst 5 containing 25% of Ni, 8% of Cu, 1% of Pd, 2% of Sn and 2% of Mo was obtained.

EXAMPLE 6

74.5 g of alumina extrudated article (each article has a diameter of 2 mm) were dried at 120° C. for 8 hrs and then were poured into 75 ml of nitrate impregnation solution containing 15 g of Ni, 10 g of Cu and 0.5 g of Pd, thoroughly mixed for 4 hrs at room temperature. After the above catalyst precursor was dried at 90° C. for 5 hrs under vacuum and was calcinated at 345° C. for 8 hrs, it was cooled, 106.7 g of catalyst 6 containing 15% of Ni, 10% of Cu and 0.5% of Pd was obtained.

EXAMPLE 7

71.5 g of alumina extrudated article (each article has a diameter of 2 mm) were dried at 120° C. for 8 hrs and then were poured into 70 ml of nitrate impregnation solution containing 20 g of Ni, 7 g of Cu, 0.5 g of Pd, 0.5 g of Nd and 0.5 g of Ce, thoroughly mixed for 4 hrs at room temperature. After the above catalyst precursor was dried at 120° C. for 8 hrs and was calcinated at 425° C. for 6 h, it was cooled, 107.5 g of catalyst 7 containing 20% of Ni, 7% of Cu, 0.5% of Pd, 0.5% of Nd and 0.5% of Ce was obtained.

EXAMPLE 8

70 g of MgO spherical carriers (each carrier has a diameter of 3 mm) were dried at 120° C. for 8 hrs and then was poured into 70 ml of nitrate impregnation solution containing 20 g of Ni, 5 g of Cu, 0.5 g of Pd, 3 g of Bi and 1.5 g of La, thoroughly mixed for 4 hrs at room temperature. After the above catalyst precursor was dried at 120° C. for 16 hrs and was calcinated at 500° C. for 6 hrs, it was cooled, 107.4 g of catalyst 8 containing 20% of Ni, 5% of Cu, 0.5% of Pd, 3% of Bi and 1.5% of La was obtained.

EXAMPLE 9

70.7 g of alumina extrudated article (each article has a diameter of 3 mm) were dried at 90° C. for 16 hrs and then were poured into 70 ml of nitrate impregnation solution containing 10 g of Ni, 15 g of Cu, 0.3 g of Pd, 1 g of Zn, 0.5 g of Mo, 0.5 g of Sn, 1.5 g of Ce, 0.3 g of La and 0.2 g of Nd, thoroughly mixed for 4 hrs at room temperature. After the above catalyst precursor was dried at 130° C. for 10 hrs and was calcinated at 470° C. for 4 hrs, it was cooled, 107.6 g of catalyst 9 containing 10% of Ni, 15% of Cu, 0.3% of Pd, 1% of Zn, 0.5% of Mo, 0.5% of Sn, 1.5% of Ce, 0.3% of La and 0.2% of Nd was obtained.

EXAMPLE 10

77.5 g of alumina extrudated article (each article has a diameter of 3 mm) were dried at 100° C. for 12 hrs and then were poured into 75 ml of nitrate impregnation solution containing 12 g of Ni, 8 g of Cu, 0.3 g of Pd, 0.5 g of V, 1 g of Fe, 0.5 g of Pb and 0.2 g of La, thoroughly mixed for 6 h at room temperature. After the above catalyst precursor was dried at 120° C. for 8 hrs and was calcinated at 450° C. for 4 hrs, it was cooled, 106.0 g of catalyst 10 containing 12% of Ni, 8% of Cu, 0.3% of Pd, 0.5% of V, 1% of Fe, 0.5% of Pb and 0.2% of La was obtained.

EXAMPLE 11

65 g of $TiO_2$ spherical carriers (each carrier has a diameter of 3 mm) were dried at 80° C. for 16 hrs and then was poured into 70 ml of nitrate impregnation solution containing 20 g of Ni, 10 g of Cu, 0.5 g of Pd, 1 g of Mn, 0.5 g of Zn, 1.5 g of Y, 1 g of W and 0.5 g of Ce, thoroughly mixed for 6 hrs at room temperature. After the above catalyst precursor was dried at 130° C. for 6 hrs and was calcinated at 425° C. for 8 hrs, it was cooled, 109.3 g of catalyst 11 containing 20% of Ni, 10% of Cu, 0.5% of Pd, 1% of Mn, 0.5% of Zn, 1.5% of Y, 1% of W and 0.5% of Ce was obtained.

EXAMPLE 12

Amination of Diglycol

A fixed bed reactor was loaded with 30 ml of bulk volume of the strip shaped catalysts 1 with a diameter of 1.5 mm for each catalyst; under 180° C., a reduction reaction was carried out with a gas mixture of 5% of hydrogen and 95% nitrogen for 12 hrs. After the reduction reaction was completed, the temperature was increased to the reaction temperature 200° C., the pressure of the system (absolute pressure, the same shall apply hereinafter) was increased to 10 MPa and the system was fed, the space velocity of diglycol was 0.3 h$^{-1}$, the molar ratio of liquid ammonia/diglycol was 20:1, the molar ratio of hydrogen/diglycol was 0.02:1, and the reactants were distilled to remove excess ammonia and water. Using gas chromatographic analysis, the content of diaminodiglycol was 77%, the content of morpholine was 16%, the content of monoaminodiglycol was 5%, diglycol was not detected, and the rest was 2%. 100 hrs after, sampling and analysing, the result did not change, the conversion of raw materials was 100%, and the yield of the aminated products was 98%.

EXAMPLE 13

Methylamination of Diglycol

A fixed bed reactor was loaded with 30 ml of bulk volume of the spherical catalysts 2 with a diameter of 3 mm for each catalyst; under 120° C., a reduction reaction was carried out with a gas mixture of 20% of hydrogen gas and 80% of nitrogen for 24 hrs. After the reduction reaction was completed, the temperature was increased to the reaction temperature 250° C., the pressure of the system was increased to 3 MPa and the system was fed, the space velocity of diglycol was 0.02 h$^{-1}$, the molar ratio of methylamine/diglycol was 5:1, the molar ratio of hydrogen/diglycol was 0.1:1, and the reactants were distilled to remove excess methylamine and water. Using gas chromatographic analysis, the content of di(methylamino)diglycol was 85%, the content of N-methylmorpholine was 8%, the content of mono(methylamino)diglycol was 4%, diglycol was not detected, and the rest was 3%. 120 hrs after, sampling and analysing, the result did not change, the conversion of raw materials was 100%, and the yield of the aminated products was 97%.

EXAMPLE 14

Dimethylamination of Diglycol

A fixed bed reactor was loaded with 30 ml of bulk volume of the spherical catalysts 3 with a diameter of 2 mm for each catalyst; under 200° C., a reduction reaction was carried out with hydrogen gas for 20 hrs. After the reduction reaction was completed, the temperature was increased to the reaction temperature 280° C., the pressure of the system was increased to 0.5 MPa the system was fed, the space velocity of diglycol was 0.05 h$^{-1}$, the molar ratio of dimethylamine/diglycol was 4:1, the molar ratio of hydrogen/diglycol was 1:1, and the reactants were distilled to remove excess dimethylamine and water. Using gas chromatographic analysis, the content of di(dimethylamino)diglycol was 92%, the content of monodimethylaminodiglycol was 5%, diglycol was not detected, and the rest was 3%. 150 hrs after, sampling and analysing, the result did not change, the conversion of raw materials was 100%, and the yield of the aminated products was 97%.

EXAMPLE 15

Amination of Dipropylene Glycol

A fixed bed reactor was loaded with 30 ml of bulk volume of the clover-type strip shaped catalysts 4 with a diameter of 3 mm for each catalyst; under 230° C., a reduction reaction was carried out with a gas mixture of 50% of hydrogen gas and 50% of nitrogen for 8 hrs. After the reduction reaction was completed, the temperature was increased to the reaction temperature 185° C., the pressure of the system was increased to 8 MPa and the system was fed, the space velocity of dipropylene glycol was 0.75 h$^{-1}$, the molar ratio of liquid ammonia/dipropylene glycol was 30:1, the molar ratio of hydrogen/dipropylene glycol was 0.05:1, and the reactants were distilled to remove excess ammonia and water. Using gas chromatographic analysis, the content of diaminodipropylene glycol was 57%, the content of dimethylmorpholine was 35%, the content of monoaminodipropylene glycol was 8%, dipropylene glycol was not detected. 100 hrs after, sampling and analysing, the result did not change, the conversion of raw materials was 100%, and the yield of the aminated products was 100%.

EXAMPLE 16

Amination of Tripropylene Glycol

A fixed bed reactor was loaded with 30 ml of bulk volume of the spherical catalysts 5 with a diameter of 3 mm for each catalyst; under 120° C., a reduction reaction was carried out with a gas mixture of 40% of hydrogen gas and 60% of nitrogen for 24 hrs. After the reduction reaction was completed, the temperature was increased to the reaction temperature 210° C., the pressure of the system was increased to 20 MPa and the system was fed, the space velocity of tripropylene glycol was 1.5 h$^{-1}$, the molar ratio of liquid ammonia/tripropylene glycol was 60:1, the molar ratio of hydrogen/tripropylene glycol was 0.2:1, and the reactants were distilled to remove excess ammonia and water. Using gas chromatographic analysis, the content of diaminotripropylene glycol was 94%, the content of monoaminotripropylene glycol was 3%, tripropylene glycol was not detected, and the rest was 3%. 150 hrs after, sampling and analysing, the result did not change, the conversion of raw materials was 100%, and the yield of the aminated products was 97%.

EXAMPLE 17

Amination of Polyether Polyol PPG-230 (Difunctional, Molecular Weight 230)

A fixed bed reactor was loaded with 30 ml of bulk volume of the strip shaped catalysts 6 with a diameter of 2 mm for each catalyst; under 150° C., a reduction reaction was carried out with a gas mixture of 20% of hydrogen gas and 80% of nitrogen for 16 hrs. After the reduction reaction was completed, the temperature was increased to the reaction temperature 230° C., the pressure of the system was increased to 25 MPa and the system was fed, the space velocity of PPG-230 was 2 h$^{-1}$, the molar ratio of liquid ammonia/PPG-230 was 40:1, the molar ratio of hydrogen/PPG-230 was 0.3:1, and the reactants were distilled to remove excess ammonia and water. Using gas chromatographic analysis, the content of the product of diamination was 97%, the content of the product of monoamination was 1%, PPG-230 was not detected, and the rest was 2%. 150 hrs after, sampling and analysing, the result did not change, the conversion of raw materials was 100%, and the yield of the aminated products was 98%.

EXAMPLE 18

Amination of Polyether Polyol T-2000 (Trifunctional, Molecular Weight 2000)

A fixed bed reactor was loaded with 30 ml of bulk volume of the strip shaped catalysts 7 with a diameter of 2 mm for each catalyst; under 250° C., a reduction reaction was carried out with a gas mixture of 5% of hydrogen gas and 95% of nitrogen for 24 hrs. After the reduction reaction was completed, the temperature was increased to the reaction temperature 300° C., the pressure of the system was increased to 30 MPa and the system was fed, the space velocity of T-2000 was 3 h$^{-1}$, the molar ratio of liquid ammonia/T-2000 was 20:1, the molar ratio of hydrogen/T-2000 was 0.01:1, and the reactants were distilled to remove excess ammonia and water. Using gas chromatographic analysis, the content of the product of tri-amination was 93%, the content of the product of di-amination was 6%, the product of mono-amination was not detected, T-2000 was not detected, and the rest was 1%. 150 hrs after, sampling and analysing, the result did not change, the conversion of raw materials was 100%, and the yield of the aminated products was 99%.

EXAMPLE 19

Amination of Polyether Polyol D-5000 (Difunctional, Molecular Weight 5000)

A fixed bed reactor was loaded with 30 ml of bulk volume of the spherical catalysts 8 with a diameter of 3 mm for each catalyst; under 130° C., a reduction reaction was carried out with pure hydrogen gas for 12 hrs. After the reduction reaction was completed, the temperature was increased to the reaction temperature 200° C., the pressure of the system was increased to 20 MPa and the system was fed, the space velocity of D-5000 was 2.5 h$^{-1}$, the molar ratio of liquid ammonia/D-5000 was 3:1, the molar ratio of hydrogen/D-5000 was 0.01:1, and the reactants were distilled to remove excess ammonia and water. Using gas chromatographic analysis, the content of the product of di-amination was 99%, the product of mono-amination was not detected, D-5000 was not detected, and the rest was 1%. 100 hrs after, sampling and analysing, the result did not change, the conversion of raw materials was 100%, and the yield of the aminated products was 99%.

EXAMPLE 20

Amination of Polyether Polyol T-403 (Trifunctional, Molecular Weight 400)

A fixed bed reactor was loaded with 30 ml of bulk volume of the strip shaped catalysts 9 with a diameter of 3 mm for each catalyst; under 175° C., a reduction reaction was carried out with pure hydrogen gas for 16 hrs. After the reduction reaction was completed, the temperature was increased to the reaction temperature 220° C., the pressure of the system was increased to 18 MPa and the system was fed, the space velocity of T-403 was 1.5 h$^{-1}$, the molar ratio of liquid ammonia/T-403 was 8:1, the molar ratio of hydrogen/T-403 was 0.02:1, and the reactants were distilled to remove excess ammonia and water. Using gas chromatographic analysis, the content of the product of tri-amination was 97%, the content of the product of di-amination was 2%, the product of mono-amination was not detected, the raw material T-403 was not detected, and the rest was 1%. 150 hrs after, sampling and analysing, the result did not change, the conversion of raw materials was 100%, and the yield of the aminated products was 99%.

EXAMPLE 21

Methylamination of Polyether Polyol D-400 (Difunctional, Molecular Weight 400)

A fixed bed reactor was loaded with 30 ml of bulk volume of the strip shaped catalysts 10 with a diameter of 3 mm for each catalyst; under 225° C., a reduction reaction was carried out with pure hydrogen gas for 24 hrs. After the reduction reaction was completed, the temperature was increased to the reaction temperature 200° C., the pressure of the system was increased to 8 MPa and the system was fed, the space velocity of D-400 was 0.3 h$^{-1}$, the molar ratio of methylamine/D-400 was 10:1, the molar ratio of hydrogen/D-400 was 0.05:1, and the reactants were distilled to remove excess methylamine and water. Using gas chromatographic analysis, the content of the product of dimethylamination was 99%, the product of monomethylamination was not detected, the raw material D-400 was not detected, and the rest was 1%. 120 hrs after, sampling and analysing, the result did not change, the conversion of raw materials was 100%, and the yield of the aminated products was 99%.

EXAMPLE 22

Dimethylamination of Polyether Polyol D-2000 (Difunctional, Molecular Weight 2000)

A fixed bed reactor was loaded with 30 ml of bulk volume of the spherical catalysts 11 with a diameter of 3 mm for each catalyst; under 250° C., a reduction reaction was carried out with pure hydrogen gas for 10 h. After the reduction reaction was completed, the temperature was increased to the reaction temperature 240° C., the pressure of the system was increased to 10 MPa and the system was fed, the space velocity of D-2000 was 0.5 h$^{-1}$, the molar ratio of dimethylamine/D-2000 was 15:1, the molar ratio of hydrogen/D-2000 was 0.03:1, and the reactants were distilled to remove excess dimethylamine and water. Using gas chromatographic analysis, the content of the product of di(dimethyl)amination was 98%, the content of the product of mono(dimethyl)amination was 1%, the raw material D-2000 was not detected, the rest was 1%. 150 hrs after, sampling and analysing, the result did not change, the conversion of raw materials was 100%, and the yield of the aminated products was 99%.

The invention claimed is:

1. A catalyst for aminating a polyether polyol, the catalyst consisting of a carrier, active components, a first promoter and a second promoter, wherein the active components are Ni, Cu and Pd; first promoter is selected from the group consisting of V, Cr, Mn, Fe, Co, Zn, Y, Mo, W, Sn, Pb and Bi elements, and a mixture thereof; and the second promoter is selected from the group consisting of La, Ce, Nd, and Sm elements, and a mixture thereof; and wherein based on the total weight of the catalyst, the content of the active components of the catalyst are as follows:

the content of Ni element is from 5 wt % to 30 wt %;
the content of Cu element is from 5 wt % to 25 wt %;
the content of Pd element is from 0.3 wt % to 2.0 wt %.

2. The catalyst according to claim 1, wherein the promoters comprise a first promoter selected from the group consisting of Co, Zn and Mo, and a mixture thereof.

3. The catalyst according to claim 2, wherein based on the total weight of the catalyst, the content of the first promoter is from 2 wt % to 4 wt %.

4. The catalyst according to claim 1, wherein based on the total weight of the catalyst, the content of the second promoter is 0.5 wt % to 1.5 wt %.

5. The catalyst according to claim 1, wherein the carrier is a porous oxide.

6. The catalyst according to claim 5, wherein the porous oxide is selected from the group consisting of MgO, Al$_2$O$_3$, SiO$_2$, TiO$_2$ and ZrO$_2$, and a mixture of thereof.

7. A preparation method of the catalyst according to claim 1 comprising the following steps:

1) impregnating the carrier with metal solutions or metal melts to obtain a catalyst precursor;
2) drying and calcinating the catalyst precursor to obtain the catalyst;
wherein the metal solutions are aqueous solutions of metal salts or aqueous solutions of metal salt complexes, the metal melts are molten metal salts, and the metals include active metals Ni, Cu and Pd; and wherein the metal further comprises a first and second promoters selected from the group consisting of V, Cr, Mn, Fe, Co, Zn, Y, Mo, W, Sn, Pb, Bi, La, Ce, Nd and Sm, and a mixture thereof.

8. The preparation method according to claim 7, wherein the drying process of step 2) is carried out at 60° C.–150° C.; the drying time is 4 hrs-24 hrs; the calcination process is carried out at 100° C.–500° C.; the calcination time is 4 hrs-24 hrs.

9. The preparation method according to claim 7, wherein the catalyst obtained in step 2) is reduced in the presence of a gas containing hydrogen gas before being used for amination of a polyether polyol, the reduction temperature is 100° C.–250° C.; the reduction time is 8 h-24 h.

10. A method for preparing polyetheramine by aminating a polyether polyol comprising the following steps:
subjecting the polyether polyol to a reductive amination reaction in the presence of a hydrogen-containing gas, an aminating agent, and the catalyst according to claim 1 to prepare the polyetheramines; and wherein the polyether polyol is a polyol comprising EO and/or PO backbone(s) with a molecular weight of 100-7000.

11. The method for preparing polyetheramines by aminating a polyether polyol according to claim 10, wherein a space velocity of the catalyst is from 0.01 to 3 liters of polyether polyol per liter of catalyst per hour.

12. The preparation method according to claim 11, wherein the drying process of step 2) is carried out at 60° C.–150° C.; the drying time is 4 hrs-24 hrs; the calcination process is carried out at 100° C.–500° C.; the calcination time is 4 hrs-24 hrs.

13. The preparation method according to claim 11, wherein the catalyst obtained in step 2) is reduced in the presence of a gas containing hydrogen gas before being used for amination of a polyether polyol, the reduction temperature is 100° C.–250° C.; the reduction time is 8 h-24 h.

14. The preparation method according to claim 8, wherein the catalyst obtained in step 2) is reduced in the presence of a gas containing hydrogen gas before being used for amination of a polyether polyol, the reduction temperature is 100° C.–250° C.; the reduction time is 8 h-24 h.

15. The catalyst according to claim 2, wherein based on the total weight of the catalyst, the content of the active components of the catalyst are as follows:
the content of Ni element is from 7 wt % to 25 wt %
the content of Cu element is from 7 wt % to 20 wt %
the content of Pd element is 0.5 wt % to 1.5 wt %.

16. The catalyst according to claim 15, wherein based on the total weight of the catalyst, the content of the active components of the catalyst are as follows:
the content of Ni element is from 10 wt % to 20 wt %;
the content of Cu element is from 8 wt % to 15 wt %.

17. The catalyst according to claim 2, wherein the promoters comprise a first promoter selected from the group consisting of Zn and Mo and a mixture thereof.

* * * * *